(12) United States Patent
Kendall

(10) Patent No.: US 10,583,124 B2
(45) Date of Patent: Mar. 10, 2020

(54) WILD BIRD TREATMENT COMPOSITION AND METHODS

(71) Applicant: Ronald J. Kendall, Ransom Canyon, TX (US)

(72) Inventor: Ronald J. Kendall, Ransom Canyon, TX (US)

( * ) Notice: Subject to any disclaimer, the term of this patent is extended or adjusted under 35 U.S.C. 154(b) by 0 days.

(21) Appl. No.: 15/053,184

(22) Filed: Feb. 25, 2016

(65) Prior Publication Data

US 2017/0246151 A1 Aug. 31, 2017

(51) Int. Cl.
*A61K 31/4184* (2006.01)
*A23K 50/70* (2016.01)
*A23K 20/111* (2016.01)
*A23K 10/30* (2016.01)
*A23K 20/137* (2016.01)

(52) U.S. Cl.
CPC .......... *A61K 31/4184* (2013.01); *A23K 10/30* (2016.05); *A23K 20/111* (2016.05); *A23K 20/137* (2016.05); *A23K 50/70* (2016.05)

(58) Field of Classification Search
CPC .. A61K 31/4184; A23K 10/30; A23K 20/137; A23K 20/111; A23K 50/70
See application file for complete search history.

(56) References Cited

U.S. PATENT DOCUMENTS

| | | | | |
|---|---|---|---|---|
| 4,000,300 | A * | 12/1976 | Mitrovic | A61K 31/415 514/388 |
| 5,260,089 | A * | 11/1993 | Thornberg | A23K 10/38 426/489 |
| 6,572,903 | B1 * | 6/2003 | Fuhr | A61K 31/415 426/72 |
| 2008/0113920 | A1 * | 5/2008 | Yang | A01N 25/10 514/22 |
| 2012/0021089 | A1 * | 1/2012 | Lush | A23K 40/20 426/2 |
| 2014/0004195 | A1 * | 1/2014 | Fahrenholz | A23K 40/10 424/489 |

OTHER PUBLICATIONS

Stephen R. Schultz, Robert X. Barry, Will A. Forbes and Mark K. Johnson, "Efficacy of Fenbendazole against Gastrointestinal Nematodes in White-Tailed Deer," Journal of Range Management, vol. 46, No. 3 (May 1993), pp. 240-244.

* cited by examiner

*Primary Examiner* — Jianfeng Song
(74) *Attorney, Agent, or Firm* — Matheson Keys & Kordzik PLLC; Jerry M. Keys; Susan M. Maze

(57) ABSTRACT

Compositions, methods of preparing compositions, and methods of treating parasitic nematode infections in wild birds include a fenbendazole premix and a grain formulation. The fenbendazole premix includes fenbendazole, a solvent, a solubilizing agent, and a premix grain carrier. The grain formulation includes a plurality of grains selected from the group consisting of ground corn, soybean meal, whole milo, wheat midds, and rice bran. The fenbendazole premix is integrated within the grain formulation thereby yielding a fenbendazole concentration in the composition of between 80 ppm and 120 ppm. Processes and methods of preparation include mixing the fenbendazole premix and grain formulation in an industrial ribbon mixer, fully integrating the fenbendazole within the grain formulation. Methods of treating include collecting and testing samples, determining a number and location of treatment systems, and charging a feeder with the claimed composition.

12 Claims, 7 Drawing Sheets

WILD BIRD TREATMENT COMPOSITION AND METHODS

CROSS-REFERENCE TO RELATED APPLICATION

This application hereby incorporates by reference U.S. patent application Ser. No. 14/543,656, filed Nov. 17, 2014, entitled WILD BIRD TREATMENT SYSTEM AND METHODS, published as US Patent Publication 20150264893 A1 on Sep. 24, 2015.

FIELD OF INVENTION

This application concerns treatment of parasitic nematode infections, and more particularly to compositions, preparations, and methods of treatment for effectively treating parasitic nematode infections in wild birds.

BACKGROUND

Historically, *Colinus virginianus* ("bobwhite quail"), a wild bird, have thrived throughout the Rolling Plains ecoregion of West Texas where they are a valuable economic species. Since 2010, wild bobwhite quail have experienced a historic decline in the Rolling Plains ecoregion. In the past, such declines in the bird population have been attributed to multiple causes, including drought, but the actual cause was not known. Results from recent research suggest that the historic decline may be the result of parasites in the wild bobwhite quail population.

Compositions, preparation methods, and treatment methods are herein disclosed for treating wild birds in their natural habitat for parasites and disease. More specifically, the compositions and methods herein disclosed are for treating wild bobwhite quail with an anthelmintic feed for preventing and controlling parasitic nematode infections.

As used herein the term "wild bird" and any conjugation thereof means and refers to any bird of a species that is living in nature without significant human control or care. Non-limiting examples include *Colinus virginianus*, members of orders Passeriformes and Galliformes, and *Callipepla squamata*.

As used herein the term "parasite," and any conjugation thereof, means and refers to a species or organism that survives in or on another living organism (the "host"), causing harm to the host while doing so. Non-limiting examples include *Oxyspirura petrowi, Aulonocephalus* spp., *Heterakis* spp., and *Capillaria* spp.

As used herein the term "roughage products," and any conjugation thereof, means and refers to harvested plants having a high concentration of slowly degradable fiber suitable for use as an animal feed ingredient. A non-limiting example includes rice hulls.

As used herein the term "about" means+/−20%.

SUMMARY

Briefly, novel compositions, methods of preparation, and methods for treating anthelmintic infections in wild birds are provided.

According to an embodiment of the present invention, a composition for the treatment of parasitic nematode infections in wild birds includes a fenbendazole premix and a grain formulation. The fenbendazole premix includes fenbendazole, a solvent, a solubilizing agent, and a premix grain carrier. The grain formulation includes a plurality of grains selected from the group consisting of ground corn, soybean meal, whole milo, wheat midds, and rice bran. The fenbendazole premix is integrated within the grain formulation thereby yielding a fenbendazole concentration in the composition of between 80 ppm and 120 ppm.

In another aspect, a product for the treatment of parasitic nematode infections in wild birds includes a fenbendazole premix and a grain formulation. The fenbendazole premix includes fenbendazole, a solvent, a solubilizing agent, and a premix grain carrier. The grain formulation includes a plurality of grains selected from the group consisting of ground corn, soybean meal, whole milo, wheat midds, and rice bran. The product is prepared by a process that includes mixing the fenbendazole premix and grain formulation in an industrial ribbon mixer to form a mixture. The mixing fully integrates the fenbendazole within the grain formulation, yielding a fenbendazole concentration in the product of between 80 ppm and 120 ppm.

In another aspect, a method of preparing a composition for the treatment of parasitic nematode infections in wild birds includes mixing a fenbendazole premix and a grain formulation in an industrial ribbon mixer. The fenbendazole premix includes a solvent, a solubilizing agent, and a premix grain carrier. The grain formulation includes a plurality of grains selected from the group consisting of ground corn, soybean meal, whole milo, wheat midds, and rice bran. The mixing fully integrates the fenbendazole within the grain formulation, yielding a fenbendazole concentration in the composition of between 80 ppm and 120 ppm.

In a further aspect, a method of treating parasitic nematode infections includes collecting at least one sample from at least one targeted wild bird from a targeted area of a natural habitat having a plurality of targeted wild birds. At least one sample is tested to determine if the targeted birds are infected with parasites or another disease. The method includes determining the number of and location of treatment systems to be installed at sites in the targeted area that are needed to treat the plurality of targeted wild birds in the targeted area. Each treatment system includes a feeder suitable for holding a composition suitable for the targeted birds. The method includes charging the feeder with the composition to treat the targeted wild birds. The composition includes a fenbendazole premix and a grain formulation. The fenbendazole premix includes fenbendazole, a solvent, a solubilizing agent, and a premix grain carrier. The grain formulation has a plurality of grains selected from the group consisting of ground corn, soybean meal, whole milo, wheat midds, and rice bran. The fenbendazole premix is integrated within the grain formulation, yielding a fenbendazole concentration in the composition of between 80 ppm and 120 ppm.

Other embodiments of the invention are disclosed and may be claimed.

BRIEF DESCRIPTION OF THE DRAWINGS

For a more complete understanding of one or more embodiments of the present invention and the advantages thereof, reference is now made to the following descriptions taken in conjunction with the accompanying drawings, in which.

DETAILED DESCRIPTION

Figure 1:
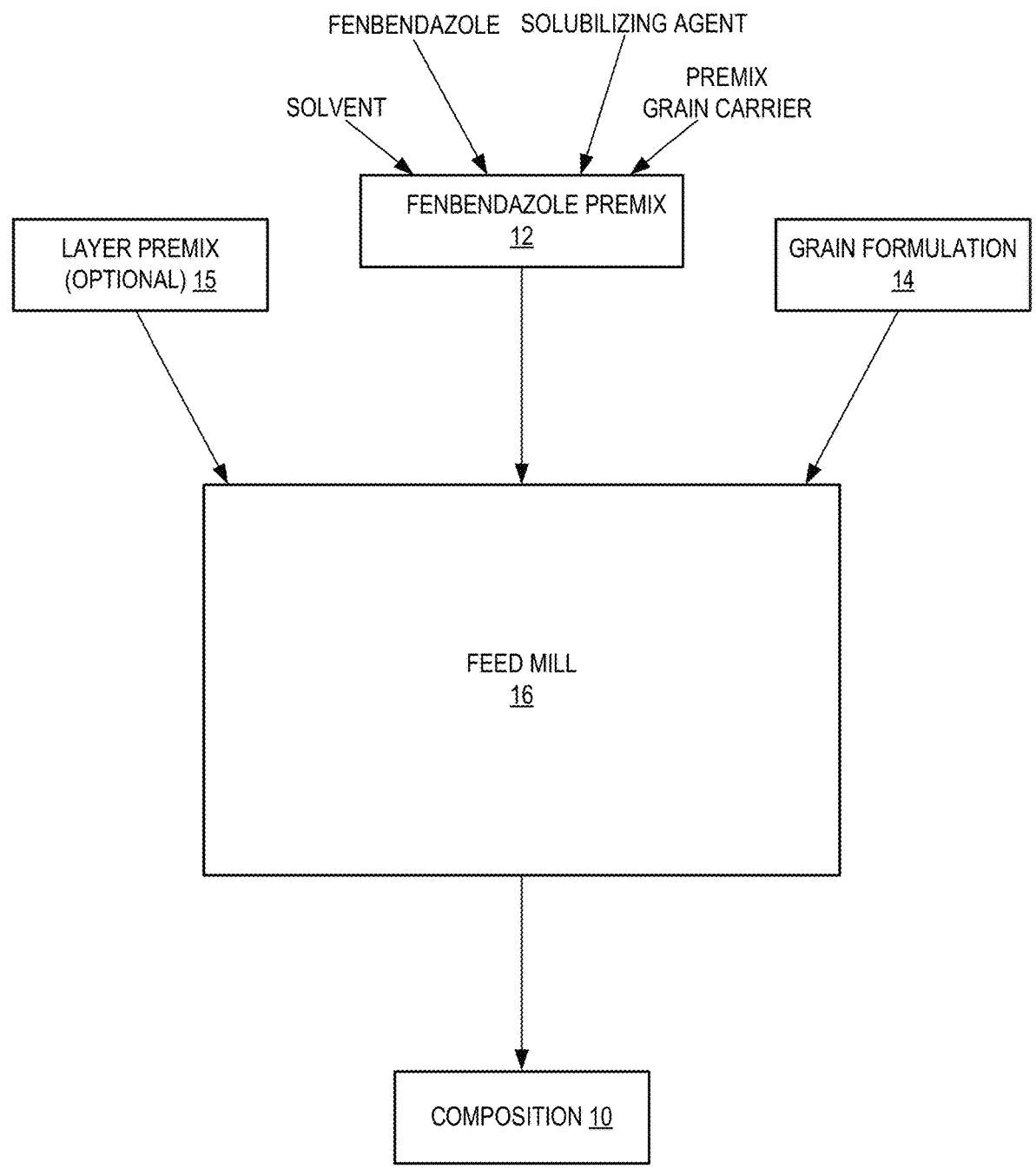
FIG. 1 is a diagram illustrating the major components of a composition useful as a feed for treating parasitic nematode infections.

*Colinus virginianus* ("bobwhite quail") of the Rolling Plains ecoregion of West Texas are infected with parasitic nematodes, including *Oxyspirura petrowi* ("eyeworm"), *Aulonocephalus* spp., *Heterakis* spp., and *Capillaria* spp. Other types of wild birds, including members of orders Passeriformes and Galliformes, and *Callipepla squamata* ("scaled quail"), may also be infected with the same or other parasitic nematodes.

Research indicates that the eyeworm is now endemic in wild bobwhite quail in the Rolling Plains ecoregion of West Texas. Further, scientific evidence indicates that as strong infections in wild bobwhite quail occur, negative impacts on the quail's survival and reproduction are probable outcomes. A medicated feed can reduce or eliminate parasitic nematode infections; however, such medicated feed must not harm the wild bobwhite quail or other wild or domesticated species.

A generalized mixing of a medication into a standard feed for domestic or farm-raised animals does not facilitate treating wild birds in a wild setting. Such a medication may break down due to ultraviolet light, heat, and other weather conditions. In addition, domestic or farm-raised animals are acclimated to eating out of feed troughs and will consume the medication quickly; whereas wild birds are not so acclimated. Therefore, the breakdown of the medication is not a concern when administering a feed based medication to domestic and farm-raised animals but is a concern when medicating wild birds.

The uncontrolled distribution of medicated feed for treating wild bobwhite quail or another targeted bird species in a natural habitat may result in such feed also being ingested by non-targeted wild and domesticated animals. This may be harmful or destructive to the non-targeted species. In addition, the treatment of diseases or parasites in wildlife with medicated feed may be subject to regulation by state and federal agencies to limit the potential harm to non-targeted species. As a result, the unrestricted distribution of medicated feed into a habitat is not advisable and may be legally prohibited pending the conduct of trial studies of the impact of medicated feed on the habitat.

Thus, compositions and methods for treating or preventing anthelmintic infections in wild birds are needed. The compositions and methods must provide good efficacy in a feed readily accepted by the wild birds, while not harming non-targeted species or the environment.

Fenbendazole is a highly effective benzimidazole class anthelmintic that is approved for use in dogs, cats, and horses as well as several food animal species, including beef and dairy cattle, goats, swine, and turkeys. Fenbendazole and related agents are commonly used for the control of nematodes. Fenbendazole is also currently approved for farm-raised pheasants (*Phasianus colchicus*) but not for any wild game bird species. Thus, the dosage level, efficacy, and toxicity of fenbendazole used for wild bobwhite quail were previously not known.

Composition

The present invention provides, in a first aspect, an anthelmintically effective composition for use as medicated feed for the treatment of wild birds. Referring to FIG. 1, major components of the composition are illustrated in a diagram. Fenbendazole premix 12, grain formulation 14, and optional layer premix 15 are inputs to feed mill 16. A preferred medicated feed for wild bobwhite quail parasitic nematode treatment, composition 10, is an output of feed mill 16. Composition 10 has a fenbendazole concentration effective in eliminating eggs, adults and immature larval stages of several parasitic species in wild bobwhite quail, including *Oxyspirura petrowi* ("eyeworm"), *Aulonocephalus* spp., *Heterakis* spp., and *Capillaria* spp, as well as other parasitic nematodes, but does not harm wild bobwhite quail.

Development of a strategy for delivering an anthelmintically effective composition for wild bobwhite quail and other wild birds requires protecting the fenbendazole, particularly from sunlight (it is prone to oxidation), heat, and other weather conditions since treatment of wild bobwhite quail and other wild birds occurs in their natural habitat. Thus, delivering treatment requires a strategy to incorporate the fenbendazole into a feed acceptable to the particular species. According to embodiments of the disclosed invention, fenbendazole is mixed and integrated into the disclosed composition in a way to protect it from sunlight, heat, and moisture, preventing breakdown of the fenbendazole and allowing it to remain available as an active ingredient in the feed for parasite control.

In certain embodiments, fenbendazole is used in the form of a powder, though other formulations may be appropriate. One of ordinary skill in the art will appreciate that the optimal concentration of fenbendazole may vary depending on the host bird species, the parasite species, and the severity of the actual or anticipated parasite challenge. Nonetheless, it has been found that typically the concentration of fenbendazole in feed administered to wild birds of order Galliformes is between 80 and 120 ppm. More typically, the fenbendazole is preferably incorporated into compositions yielding a concentration of about 100 ppm in a granule type feed for treatment of wild bobwhite quail, as is more particularly described herein below.

Fenbendazole premix 12 includes at least one component selected from each of the following groups: solvents, solubilizing agents, and premix grain carriers. In fenbendazole premix 12, a lipophilic solubilizing agent (e.g., calcium carbonate) is integrated into the matrices of powdered fenbendazole. A premix solvent (e.g., mineral oil) attaches to the solubilizing agent, distributing and stabilizing the fenbendazole throughout fenbendazole premix 12. The solubilized fenbendazole requires an effective premix grain carrier, preferably roughage products, to facilitate mixing into one ton allotments of feed. Representative fenbendazole premix 12 components are shown below in Table 1.

TABLE 1

Representative Fenbendazole Premix Components

| Solvents | Solubilizing Agents | Premix grain carriers |
|---|---|---|
| Mineral Oil | Calcium carbonate | Roughage Products |
| Soybean Oil | | Rice hulls |
| Peanut Oil | | Wheat midds |
| | | Ground corn cobb |
| | | Soybean meal |

A preferred fenbendazole premix formulation for wild bobwhite quail is shown in Table 2.

TABLE 2

Preferred Fenbendazole Premix

| Component | PPM (by weight) |
|---|---|
| Fenbendazole | 20,000 |
| Mineral, Soybean, or Peanut Oil | 30,000-50,000 |
| Calcium Carbonate | 350,000-480,000 |
| Roughage Products | 350,000-480,000 |

Once established with the right concentration of fenbendazole 20,000 ppm, fenbendazole premix 12 is integrated into grain formulation 14 as described herein below in the section titled PRODUCT BY PROCESS AND METHOD OF PREPARATION. Grain formulation 14 includes grains preferably selected from the group consisting of ground corn, soybean meal, whole milo, wheat midds, and rice bran.

In an embodiment of the present invention, a concentrated fenbendazole premix may be formulated with a fenbendazole concentration about 200,000 ppm. A preferred concentrated premix formulation is shown below in Table 3.

TABLE 3

Preferred Concentrated Premix

| Component | PPM (by weight) |
|---|---|
| Fenbendazole | 200,000 |
| Mineral, Soybean, or Peanut Oil | 30,000-50,000 |
| Calcium Carbonate | 350,000-450,000 |
| Roughage Products | 350,000-450,000 |

One part concentrated premix is then blended into nine parts premix grain carrier, preferably rice hulls, to yield fenbendazole premix 12 with a fenbendazole concentration about 20,000 ppm by weight.

In another embodiment, composition 10 also includes a layer premix 15 comprising a calcium based substrate to facilitate egg laying, increase egg production, increase hardness of the egg shell, and supply adequate nutrients for laying wild birds.

A particularly preferred composition 10 for treatment of parasitic nematode infections in wild bobwhite quail is shown Table 4 below:

TABLE 4

Preferred Composition for Wild Bobwhite Quail

| Component | PPM (by weight) |
|---|---|
| Fenbendazole Premix | 5,000 |
| Layer Premix | 12,500 |
| Ground Corn | 410,000 |
| Soybean Meal | 310,000 |
| Whole Milo | 100,000 |
| Wheat Midds | 100,000 |
| Rice Bran | 62,500 |

Composition 10 is ready for introduction into a wild bird environment and is highly palatable to the wild birds. Sampling of the treated feed composition shows excellent fenbendazole stability as discussed herein below. This is crucial to wild bobwhite quail populations because the treated feed composition will remain in feeders where the birds will access feed ad libitum.

In order to evaluate the efficacy and stability of the compositions of the invention, a number of studies were conducted using the composition of Table 4 shown above. The following non-limiting examples disclose the safety of the disclosed composition to bobwhite quail, the efficacy of 100 ppm fenbendazole compositions in treating bobwhite quail challenged with eyeworm and cecal nematode infections, and the stability of fenbendazole in the disclosed composition in a natural habitat, such as the Rolling Plains of West Texas ecoregion, for an extended period.

Example 1—Toxicity Study

Toxicity was determined in an eight week study using 48 pen-raised bobwhite quail ("treated birds") fed exclusively composition 10 containing 100 ppm fenbendazole prepared using the method of preparation disclosed herein below in the section titled: PRODUCT BY PROCESS AND METHOD OF PREPARATION. Composition 10 was provided to 40 birds with 8 birds receiving non-medicated feed ("control birds"). Feed and water was provided ad libitum for two months. In contrast, field exposure of composition 10 to wild bobwhite quail in Example 2, discussed herein below, was one month or less. Prior to starting the study birds were individually weighed and were weighed weekly thereafter. Behavior was monitored daily until the birds were euthanized. There were no mortalities in treated birds throughout the eight week study. The birds readily consumed composition 10 and showed no avoidance. In addition, no weight loss in any of the treated birds was recorded. Birds were euthanized in 2 week increments. After euthanasia, each bird was reweighed. At no time during the study were the birds behaving out of the ordinary or seeming to have experienced any toxicity from composition 10. Additionally, no significant weight loss or gain was recorded in treated birds during the study, nor did the treated birds differ in weight loss or gain in average as compared to control birds.

TABLE A

Toxicity of Composition to Bobwhite Quail

| Treatment Period | Control Bird Average Weight Gain (grams) | Treated Bird Average Weight Gain (grams) |
|---|---|---|
| 1 | 4.50 | 2.90 |
| 2 | 0.50 | 5.70 |
| 3 | 0.25 | 2.86 |
| 4 | 7.50 | 7.00 |

Conclusion: Composition 10 containing 100 ppm fenbendazole was shown to be non-toxic to pen-raised bobwhite quail fed exclusively on composition 10 for eight weeks. A method of treatment disclosed herein below includes a treatment period of three weeks.

Example 2—Efficacy Study

The object of the below described study was to evaluate the effect of composition 10 in wild bobwhite quail. The study was conducted over two years at two sites in the Rolling Plains ecoregion of West Texas. Site I is approximately 6,000 acres and is located in Stonewall County, Tex. with a mean annual daily temperature ranging from −1° C. in January to 37° C. in July and average annual precipitation of 57 cm per year. The second site, Site II, is approximately 120,000 acres and is in Mitchell County, Tex., with a mean annual daily temperature ranging from 0° C. in January to 36° C. in July and average annual precipitation of 50 cm per year. Both sites are privately owned cattle ranches.

Figure 7:
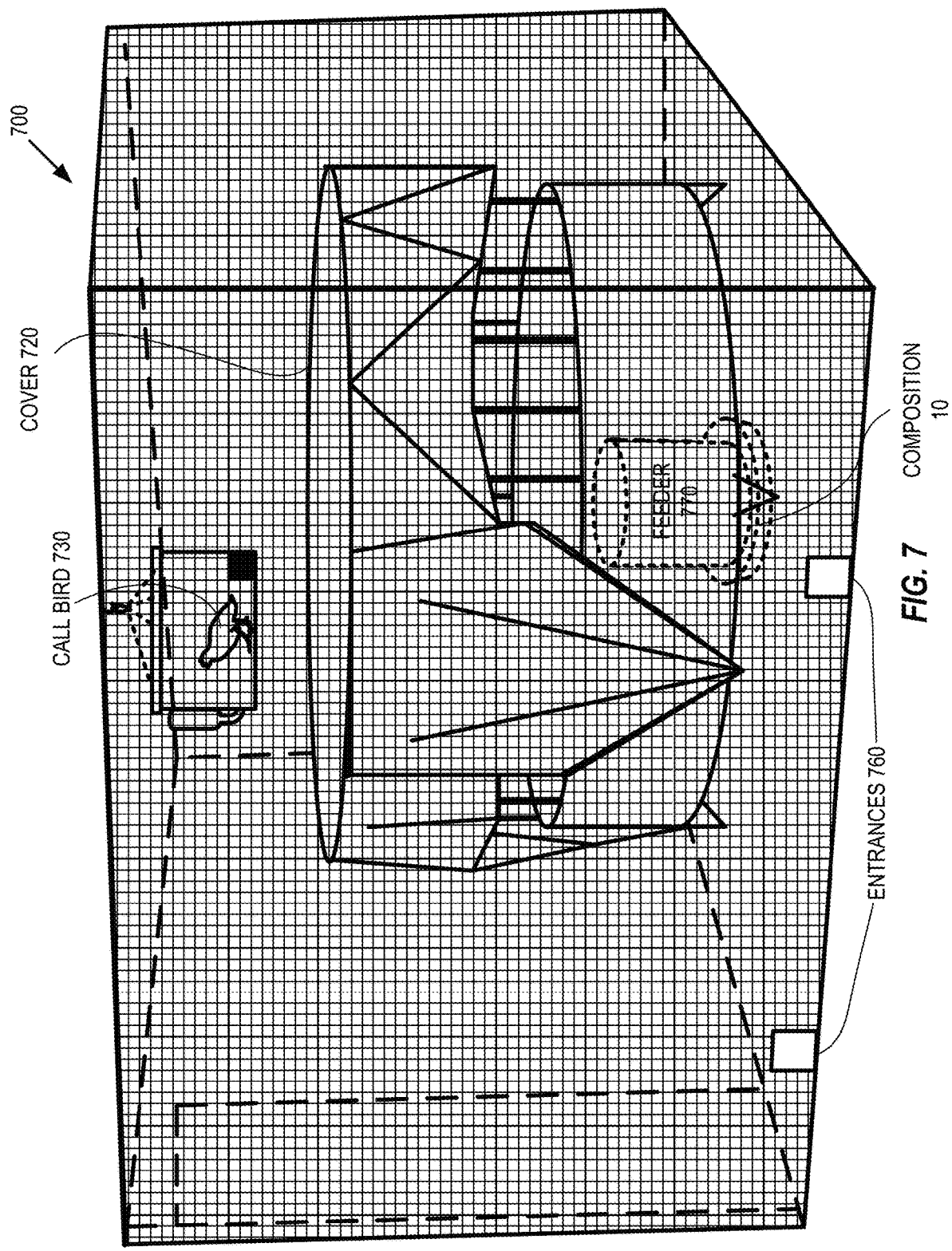
FIG. 7 illustrates an isometric view of an embodiment of an exemplary system used for treating parasitic nematode infections with the composition, according to embodiments of the present invention.

Referring to FIG. 7, a wild bird treatment system 700, disclosed in U.S. Patent Application Publication No. 20150264893 A1, published Sep. 24, 2015, is depicted, including an enclosure with ground entrances 760 and feeder 770. Feeder 770 is depicted protected by a suitable cover 720 which may be a tarp, for example, such that composition 10 is not blown outside the system 700. System 700 is large enough that a covey or multiple coveys of quail or other targeted wild birds may enter with adequate available space.

Figure 8:
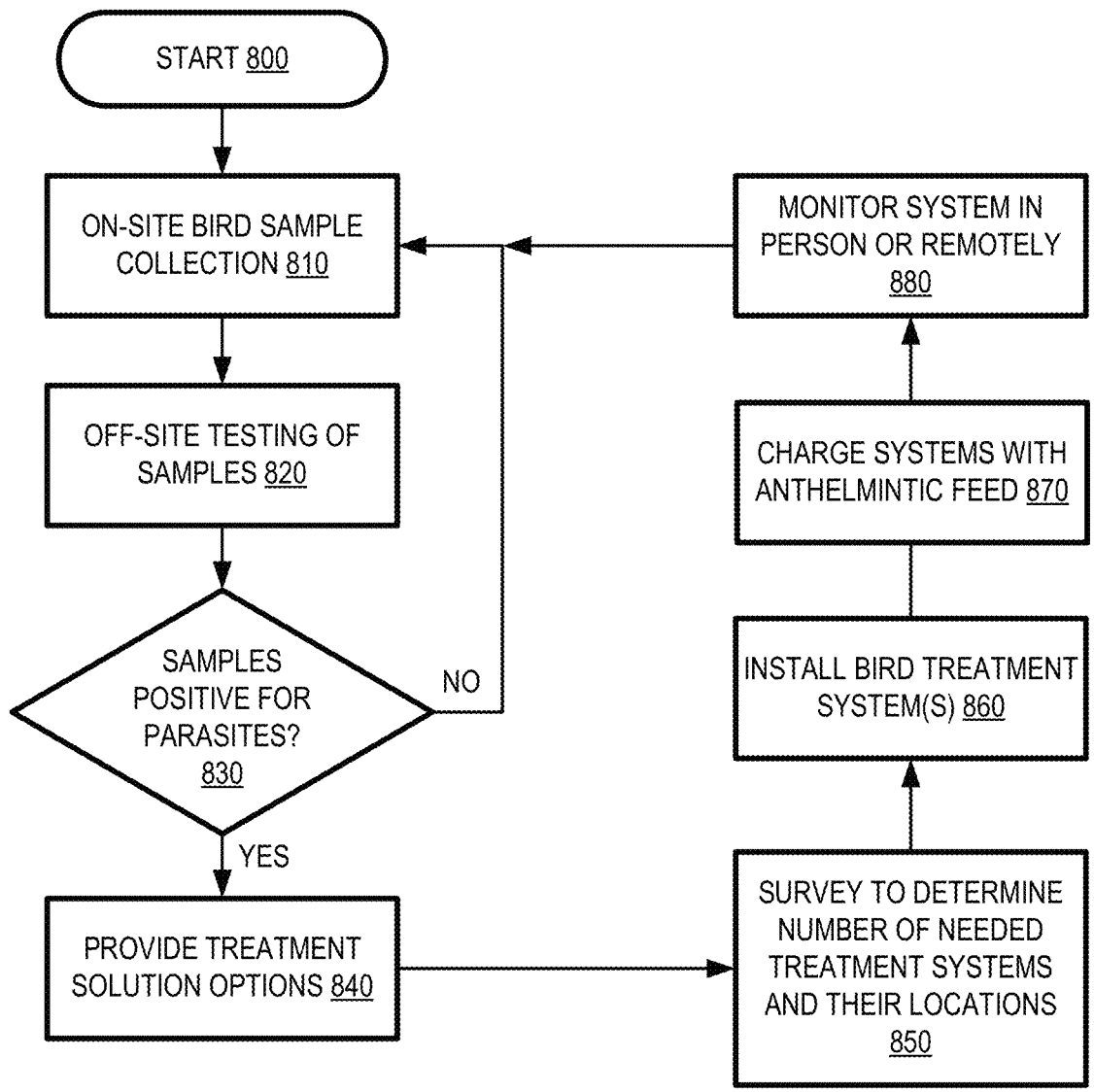
FIG. 8 is a flow chart diagram illustrating a method of treating parasitic nematode infections, according to embodiments of the present invention.

Referring to FIGS. 7 and 8, in an embodiment, systems 700 using composition 10 ("treatment systems") and systems using non-medicated feed ("control systems") were deployed at field sites at least 1 mile apart and accessible for wild bobwhite quail to enter and exit. Composition 10 or non-medicated feed ("control feed"), was deposited in feeder 770, and placed in the approximate center of the systems.

An infrared trail camera was placed in the corner of each system 700 to observe wildlife visitation. System 700 was designed to successfully eliminate entry from quail predators including raccoons (*Procyon lotor*), red-tailed hawks (*Buteo jamaicensis*), northern harriers (*Circus cyaneus*), Cooper's hawk (*Accipiter cooperii*), wild boar (*Sus scrofa*) and coyotes (*Canis latrans*), creating a safe zone for wild bobwhite quail to eat. As a result, there was no evidence of quail mortality inside or around the field study systems 700.

Wild bobwhite quail were trapped after field study periods and transported to a Wildlife Toxicology Lab's Aviary at Texas Tech University. Each bird was held in an individual 256.6 cm cage prior to necropsy and given water and control feed ad libitum. While the birds were being housed, feces was collected and sampled to check for any nematode infections.

Euthanization occurred within 24 hours of returning wild bobwhite quail to the aviary, using carbon dioxide followed by cervical dislocation in accordance with standard protocols. Prior to performing the necropsy, quail weight, sex, and age were identified. Then, a cecal swab sample was taken from each bird for the detection of nematode eggs shed in feces.

To initiate the necropsy, the head was first separated and examined for eyeworm. Next, a small incision was made to open the body cavity and the cecum was removed. The removed cecum was examined for cecal nematodes by removing individual specimens to calculate worm burdens. Both eyeworms and cecal nematodes from each individual bird were stored separately in a vial filled with 70% ethanol for morphological identification. Additionally, the brain, breast, and liver were sampled and stored in 10% formalin for histology analysis. A body condition score was noted for comparison among the control and treated birds. Body conditions also provide an idea on how different habitats (Site II vs Site I) can provide a different quality of body condition.

Overall body condition scores (scale of 1-5, 5 being extensive fat reserves) for wild bobwhite quail were taken into account (Tables B1 and B2, below). Body condition scores between 3 and 4 are considered the healthiest of birds.

First Field Study

A First Field Study included twelve systems 700, six at Site I and six at Site II. An acclimation period of two weeks was allowed for quail to begin adjusting to the systems. During this acclimation period, only control feed was dispensed. The acclimation period was followed by a four week treatment period.

During the treatment period, composition 10 was randomly assigned to half of systems 700 while the remaining half were control systems assigned control feed. Twice per week, composition 10 and control feed was replaced with fresh feed and measured. Composition 10 was removed four weeks before the hunting season started (late October) and replaced with control feed.

A total of five wild bobwhite quail were captured from control systems and eleven were captured from treatment systems at Site I. A total of ten control and twelve treated birds were captured from Site II. More than 75% of the birds captured were juveniles. Only one scaled quail was captured from Site II. A total of 7 females and 9 males were collected from Site I, and a total of 8 females and 14 males were collected from Site II. Field study protocol allowed for 24 birds to be trapped and collected from each field site. However, an unexpected amount of rainfall near the early fall trapping period facilitated increased food sources for quail and trapping was more subdued than expected.

TABLE B1

First Field Study Results Average (±Standard Deviation) body weight and condition for control versus treated wild bobwhite quail at Sites I and II

| | Average control body weight (grams) | Average control bird condition | Average treated body weight (grams) | Average treated body condition |
|---|---|---|---|---|
| Site I | 140 ± 15.94 | 2.8 ± 0.45 | 147 ± 11.16 | 3.27 ± 0.65 |
| Site II | 139 ± 9.55 | 2.4 ± 0.52 | 139 ± 19.82 | 2.83 ± 0.72 |

Second Field Study

A second field study, did not include an acclimation period, and included a treatment period of two weeks at Site II and three weeks at Site I. The second field study included 24 systems 700, twelve at Site I and twelve and Site II. Site II was an experimental site, while Site I was a demonstration site only, maintained by the ranch owner and manager to confirm the manageability of the disclosed composition and systems by those not skilled in the art.

Composition 10 was randomly assigned to half of systems 700 while the remaining half was assigned control feed, with the exception of Site I (assigned composition 10 only). Twice per week, the feed was replaced with fresh composition 10 or control feed and measured. Feedback weight, the amount of feed consumed at feeder in an allotted time (4 days), was recorded for both. Approximately five grams of the feedback was sampled from systems 700 weekly to analyze any potential fenbendazole breakdown within composition 10. Composition 10 was removed four weeks before the hunting season started (late October) and replaced with control feed. At Site II, a total of eleven control and twelve treated birds were captured. Of those birds, eight were female and fifteen were male.

TABLE B2

Second Field Study Results Average (±Standard Deviation) body weight and condition for control versus treated wild bobwhite quail at Site II

|  | Average control body weight (grams) | Average control bird condition | Average treated body weight (grams) | Average treated bird body condition |
|---|---|---|---|---|
| Site II | 147 ± 12.71 | 3.23 ± 0.47 | 155 ± 15.34 | 3.17 ± 0.39 |

Eyeworms

Treated and control birds were compared for eyeworm prevalence. First Field Study (Table C1) at Site II had 80% of control birds infected with eyeworms, ranging from a total of 1-46 per bird. Only 17% of treated birds at Site II had eyeworms, ranging from a total of 0-22 per bird. First Field Study Site I had a low number of control birds collected (as mentioned above), however 60% of those birds were infected with the eyeworm, ranging from 0-5 per bird; whereas treated birds had a 36% infection rate with eyeworms, ranging from 0-8 per bird.

TABLE C1

First Field Study Results Eyeworm infection for control versus treated wild bobwhite quail at Sites I and II

|  | % Ctrl infected | % Treated infected |
|---|---|---|
| Site I | 60% | 36% |
| Site II | 80% | 17% |

For the Second Field Study (Table C2), treated feed was dispensed for only half the time (2 weeks) as in the First Field Study. Site II had 91% of control birds infected with eyeworms (ranging from 1-53 eyeworms per bird). At Site II, 83% of treated birds had dead or dying eyeworms, suggesting strong fenbendazole efficacy. 7% of treated birds at Site II had no eyeworms.

TABLE C2

Second Field Study Results Eyeworm infection for control versus treated wild bobwhite quail at Site II

|  | % Ctrl infected | % Treated infected |
|---|---|---|
| Site II | 91% | 0% |

Cecal Nematodes

Cecal nematodes during Field Study 1 at Site II were controlled extremely well when quail were consuming composition 10 (Table D1). Only one quail from a treated system was found to be infected with cecal nematodes, totaling 592, and could represent an outlier that had just arrived to feed the day it was caught. Nevertheless, after two years of research at Site II, to find any quail not infected with cecal nematodes was highly unusual. Similarly during the First Field Study at Site I, cecal nematodes were extremely well controlled by wild bobwhite quail consumption of composition 10, although it was not unexpected to have at least some outliers raising the average cecal nematode count within treatment systems due to the removal of composition 10 two weeks before the last three birds were caught for analysis. In this case, only one outlier was from a bird with 484 cecal nematodes in one cecum. This bird may have only recently arrived to feed on composition 10 because of the excessive rainfall delaying capture of those treated birds from the ranch. Nevertheless, on both Site II and Site I wild bobwhite quail were free of cecal nematode infection when consuming composition 10.

TABLE D1

First Field Study Results Cecal nematode infection and average (±Standard Deviation) parasite load for control versus treated wild bobwhite quail at Sites I and II

|  | % Ctrl infected | Average ctrl parasite load (per bird) | % Treated infected | Average treated parasite load (per bird) |
|---|---|---|---|---|
| Site I | 60% | 28 ± 43.23 | 16% | **49 ± 145.20 |
| Site II | 40% | 86 ± 124.07 | 9% | *50 ± 770.90 |

*Only one treated quail was recorded to have cecal nematodes (592), remaining birds had 0 cecal infections.
**Only two treated quail had cecal nematodes (50 and 484) and remaining birds had 0 cecal infection.

For the Second Field Study (Table D2), treated feed was dispensed for only half the time (2 weeks) as in the First Field Study. Site II had 100% of control birds infected with cecal nematodes. Only 42% of treated birds at Site II had cecal nematodes.

TABLE D2

Second Field Study Results Cecal nematode infection and average (±Standard Deviation) parasite load for control versus treated wild bobwhite quail at Site II

|  | % Ctrl infected | Average ctrl parasite load (per bird) | % Treated infected | Average treated parasite load (per bird) |
|---|---|---|---|---|
| Site II | 100% | 149 ± 99.50 | 42% | 18 ± 33.59 |

Feedback Weight

During the First Field Study, quail had two weeks to adjust to systems 700 before data was collected (this acclimation period was excluded for Field Study 2). However, visual evidence from game cameras showed that quail adjusted within a couple days of exposure. Feed was dispensed every three to four days, and any feedback weight was measured in order to account for consumption (Tables E1 and E2).

TABLE E1

First Field Study Results Average Feed (±Standard Deviation) dispensed and consumed within three to four days at Sites I and II

|  | Average feed dispensed (lbs.) | SD± | Average feed consumed (lbs.) | SD± |
|---|---|---|---|---|
| Site I | 2.26 | 0.28 | 0.58 | 0.63 |
| Site II | 2.38 | 0.34 | 1.24 | 1.09 |

TABLE E2

Second Field Study Results Average Feed (±Standard Deviation) dispensed and consumed within three to four days Site II

| | Average feed dispensed (lbs.) | SD± | Average feed consumed (lbs.) | SD± |
|---|---|---|---|---|
| Site II | 2.72 | 0.88 | 1.16 | 0.82 |

For the Second Field Study, all systems 700 were deployed before habitat green-up, which heavily increased utilization due to quail habituation of the food resource in systems 700. Field examples confirm that when quail habituate to available food resources, such as in systems 700, before habitat green-up, this is a strong attractant going forward for having quail consistently visit systems 700 looking for food. Therefore, once wild bobwhite quail are habituated to the food availability in systems 700, they can be offered treatment feed at any point throughout the year and have good success in getting feed utilization. Of the thousands of quail visits to 700 during the First and Second Field Studies, no quail deaths were observed in and around the systems. In addition, the quail remained wild in nature and showed no evidence of becoming domesticated or tolerant of human presence.

Cameras provided surveillance evidence of systems 700, day or night. The surveillance evidence showed that raccoons and hogs were unable to enter systems 700. Daily visitation, in addition to quail, included very limited song birds, doves, rabbits, ground squirrels, field mice, and an occasional roadrunner (*Geococcyx californianus*). Of the non-target species, very few consumed any food if at all. However, >90% of the species that visited systems 700 were wild bobwhite quail. Quail entered systems 700 individually or in groups of two to thirty birds at a time. It is expected that larger sized coveys will enter systems 700 as quail are habituated to the food resource.

Wildlife Toxicology Laboratory data from Site II showed higher infection rates among quail populations three to six miles from systems 700. As part of another Wildlife Toxicology Laboratory ongoing study at Site II, sampled quail are found to be 100% infected with cecal nematodes, 97% of adults infected with eyeworm, and 92% of juveniles infected with eyeworm. An additional Wildlife Toxicology Laboratory study found 100% infection with both the cecal nematodes and eyeworm in birds. Radio telemetry data on these nearby sites, show quail stay within a close proximity to their home range showing quail remain close to systems 700, but remain wild.

Birds free of nematode parasites, from both Sites I and II were found only in treatment systems consuming composition 10. Parasitic nematodes recovered from quail that accessed treatment systems appear to be impaired after two weeks, and by four weeks the parasitic nematodes passed from the bird (0 infections). Therefore, a composition 10 treatment period of approximately three weeks will allow time for the parasitic nematodes to not only appear moribund but also be eliminated from the bird.

Conclusion: Excellent control (reduction of eyeworm burden >90% and reductions of cecal nematode burden >95%) was achieved using composition 10 at the conclusion of Field Studies.

Example 3—Stability Study

To test for stability, fenbendazole concentration in composition 10 was analyzed in field conditions in 4 day blocks. Further, integration of fenbendazole into composition 10 was analyzed to determine integration of fenbendazole into feed granules, and composition 10 was tested under elevated temperature conditions.

Stability Test Analysis Method

The stability of fenbendazole in composition 10 was analyzed by extracting fenbendazole from feed samples using a mixture of water and acetonitrile. A 65:35 Acetonitrile and Ammonium acetate buffer was used as a mobile phase. Ammonium acetate buffer was prepared by dissolving 3.854 gm of ammonium acetate in a liter of water. The pH was adjusted to 5 using acetic acid. Fenbendazole stock standard was prepared in a 50:50 mixture of dimethyl sulfoxide and methanol. All intermediate standards were prepared in methanol and the working standards are prepared in acetonitrile.

Extraction of fenbendazole from feed samples was performed by a slight modification of dilute-and-shoot method. Briefly, 5 ml of water was added to 2.5 gm of ground/powdered feed samples and the mixture was vortexed for 5 minutes. After soaking for an hour, 15 ml of acetonitrile was added to the mixture. The mixture was again vortexed for 10 minutes followed by centrifugation at 5000 rpm for 10 minutes. The supernatant was filtered through a 0.45 um filter and loaded on to an autosampler.

The amount of fenbendazole in feed samples was quantitated by two different methods: 1) External standard calibration (ESC) method and 2) Matrix-Matched calibration (MMC) method. To quantitate samples using an ESC method, an ESC curve was generated using the response from a range of concentrations of Fenbendazole (0, 1, 3, 5, 10, and 15 ppm). The response (peak area) from a fixed injection volume of 10 ppm standard injected amidst every five samples is used to quantitate the concentration of fenbendazole in feed extracts using formula 1.

$$\text{Concentration}_{unknown} = (\text{Area}_{unknown}/\text{Area}_{known}) \times \text{Concentration}_{known}$$

MMC is a process of ESC in which calibration standards are added to the sample matrix. MMC curve was developed by spiking blank feed samples with known concentration of fenbendazole (0.125, 0.375, 0.625, 1.250, 2.500, 5.000, 7.500, 10.000 and 12.500 ppm). Using an external MMC compensates for the suppression/enhancement of signal from the analytes in the presence of matrix components thereby increasing the accuracy in the results.

Linearity of method was evaluated by performing a regression analysis of the response from ESC and MMC standards of fenbendazole as a function of concentration. Method recoveries were determined at three levels of fortification of untreated feed samples: 10, 20 and 50 ppm (Table I). It is measured by comparing the response from fortified and extracted feed samples to the response obtained from pure standards.

Method detection limit (MDL) and method quantitation limit (MQL) were calculated using a procedure described by the U.S. Environmental Protection Agency. 10 replicates of a 3 ppm standard were analyzed against the calibration curve to determine the method detection and quantitation limits.

Precision and accuracy examples were carried out by replicate analysis of known concentrations of fortified control feed samples (10, 20 and 50 ppm) according to the guidelines specified by the Food and Drug Administration for bioanalytical method validation (Tables II and III). 10 replicates per concentration were analyzed to determine the intra-day precision and 3 replicates were analyzed for 5 consecutive days to determine inter-day precision. Precision and accuracy were determined as % coefficient of variance (% CV) or relative standard deviation (RSD).

Both ESC and MMC curve used to quantitate fenbendazole in feed extracts demonstrated excellent linearity (r2 of 0.999 and 0.998 respectively).

Method Detection Limits (MDL) and Method Quantitation Limits (MQL)

MDL of ESC method: 0.51 ppm
MQL of ESC method: 1.81 ppm
MDL of MMC method: 0.36 ppm
MQL of MMC method: 1.28 ppm

TABLE I

Recoveries

| Concentration (ppm) | Recovery1 | % Recovery1 | Recovery2 | % Recovery2 |
|---|---|---|---|---|
| Level 1: 10 | 10.47 (0.35) | 104.7 ± 3.46 | 8.85 (0.24) | 88.5 ± 2.41 |
| Level 2: 20 | 20.32 (1.25) | 101.6 ± 6.24 | 15.72 (0.87) | 78.6 ± 4.35 |
| Level 3: 50 | 48.83 (2.21) | 97.7 ± 4.45 | 36.62 (1.55) | 71.24 ± 3.10 |

Note:
Recovery of fenbendazole (ppm) in feed samples obtained from ESC; 2. Recovery of fenbendazole (ppm) in feed samples obtained from MMC; n = 3 and values in parenthesis represent one standard deviation from the mean.

TABLE II

Intra-day and Inter-day Precision and Accuracy ESC

| Target concentration (ppm) | Intra-day precision (ESC) | | | | Inter-day precision (ESC) | | | |
|---|---|---|---|---|---|---|---|---|
| | n | Measured concentration (Mean ± SD) | % CV | % accuracy | n | Measured concentration (Mean ± SD) | % CV | % accuracy |
| 10 | 10 | 10.14 ± 0.36 | 3.52 | 101.4 | 3 | 10.18 ± 0.09 | 0.84 | 101.8 |
| 20 | 10 | 19.91 ± 1.91 | 9.58 | 99.5 | 3 | 20.42 ± 1.60 | 7.83 | 102.1 |
| 50 | 10 | 49.48 ± 0.75 | 1.52 | 98.9 | 3 | 49.53 ± 0.59 | 1.18 | 99.06 |

TABLE III

Intra-day and Inter-day Precision and Accuracy MMC

| Target concentration (ppm) | Intra-day precision (MMC) | | | | Inter-day precision (MMC) | | | |
|---|---|---|---|---|---|---|---|---|
| | n | Measured concentration (Mean ± SD) | % CV | % accuracy | n | Measured concentration (Mean ± SD) | % CV | % accuracy |
| 10 | 10 | 9.03 ± 0.26 | 2.86 | 90.3 | 3 | 9.07 ± 0.06 | 0.70 | 90.7 |
| 20 | 10 | 16.10 ± 1.38 | 8.58 | 80.5 | 3 | 16.48 ± 1.15 | 7.01 | 82.4 |
| 50 | 10 | 37.52 ± 0.54 | 1.45 | 75.0 | 3 | 37.56 ± 0.42 | 1.12 | 75.1 |

Stability Test 1—Composition 10 Fenbendazole Concentration in Field Conditions for Duration of 4 Days For the purpose of this study, composition 10 was randomly assigned to 6 different feeder systems, 3 at Site II and 3 at Site I. The feed was replaced twice per week. This meant that composition 10 replaced every 4 days. Remaining composition 10 was bought back to the lab and stored in a refrigerator until the time of analysis.

Daily temperatures and amount of fenbendazole extracted from composition 10 samples after a duration of 4 days in field conditions are included in Table IV.

TABLE IV

Fenbendazole Concentration after 4 days with Site Temperature

| Date | Sampling Period | Temperature (° C.) | Sample ID | Fenbendazole[1] % ESC curve | Fenbendazole[2] % MMC curve |
|---|---|---|---|---|---|
| Aug-18 | 1 | 29 | 2T | 82.83 | 61.6 |
| | | | 4T | 86.06 | 64.0 |
| | | | 6T | 58.82 | 44.2 |
| | | | 8T | 60.73 | 45.6 |
| | | | 10T | 59.55 | 44.8 |
| | | | 11T | 87.99 | 65.4 |
| Aug-22 | 2 | 29 | 2T | 78.88 | 58.8 |
| | | | 4T | 6.03 | 5.75 |
| | | | 6T | 87.88 | 65.3 |
| | | | 8T | 97.15 | 72.0 |
| | | | 10T | 61.22 | 46.0 |
| | | | 11T | 89.51 | 66.5 |
| Aug-26 | 3 | 38 | 2T | 81.84 | 60.9 |
| | | | 4T | 79.91 | 59.5 |
| | | | 6T | 80.82 | 60.2 |
| | | 35 | 8T | 46.29 | 35.1 |
| | | | 10T | 71.25 | 53.2 |
| | | | 11T | 81.40 | 60.6 |
| Aug-29 | 4 | 29 | 2T | 100.65 | 74.5 |
| | | | 4T | 49.99 | 36.41 |
| | | | 6T | 67.34 | 50.4 |
| | | 29 | 8T | 22.39 | 17.8 |
| | | | 10T | 17.51 | 14.3 |
| | | | 11T | 15.91 | 13.1 |
| Sep-02 | 5 | 38 | 2T | 67.29 | 50.4 |
| | | | 4T | 84.84 | 63.1 |
| | | | 6T | 67.41 | 50.5 |
| | | 38 | 8T | 86.03 | 63.9 |
| | | | 10T | 67.89 | 50.8 |
| | | | 11T | 67.98 | 50.9 |
| Sep-05 | 6 | 35 | 2T | 104.38 | 74.33 |
| | | | 4T | 107.41 | 76.45 |
| | | | 6T | 107.80 | 76.72 |
| | | 35 | 8T | 68.70 | 51.4 |
| | | | 10T | 97.61 | 72.3 |
| | | | 11T | 97.37 | 72.2 |
| Sep-08 | 7 | 31 | 2T | — | — |
| | | | 4T | 71.24 | 53.2 |
| | | | 6T | 53.45 | 40.3 |
| | | 31 | 8T | 60.93 | 45.8 |
| | | | 10T | 74.12 | 55.3 |
| | | | 11T | 55.33 | 41.7 |
| Sep-11 | 8 | 26 | 2T | 95.09 | 70.5 |
| | | | 4T | 68.85 | 51.5 |
| | | | 6T | 88.77 | 63.45 |
| | | 19 | 8T | 18.34 | 14.9 |
| | | | 10T | 85.57 | 63.6 |
| | | | 11T | 84.19 | 62.6 |
| Sep-16 | 9 | 28 | 2T | 51.46 | 38.9 |
| | | | 4T | 46.05 | 35.0 |
| | | | 6T | 79.52 | 59.2 |
| | | 18 | 8T | 83.90 | 62.4 |
| | | | 10T | −0.13 | — |
| | | | 11T | 54.10 | 40.8 |
| Sep-18 | 10 | 25 | 2T | 79.77 | 59.4 |
| | | | 4T | 72.75 | 54.3 |
| | | | 6T | 76.91 | 57.3 |
| | | 28 | 8T | — | — |
| | | | 10T | 40.25 | 30.8 |
| | | | 11T | 55.09 | 41.5 |
| Sep-22 | 11 | 26 | 2T | 95.60 | 70.9 |
| | | | 4T | 85.61 | 63.6 |
| | | | 6T | 90.13 | 66.9 |
| | | 24 | 8T | 76.88 | 57.3 |
| | | | 10T | 79.72 | 59.4 |
| | | | 11T | 84.05 | 62.5 |
| Sep-25 | 12 | | 2T | — | — |
| | | | 4T | — | — |
| | | | 6T | — | — |

TABLE IV-continued

Fenbendazole Concentration after 4 days with Site Temperature

| Date | Sampling Period | Temperature (° C.) | Sample ID | Fenbendazole[1] % ESC curve | Fenbendazole[2] % MMC curve |
|---|---|---|---|---|---|
| | | 28 | 8T | 78.43 | 58.4 |
| | | | 10T | 97.69 | 72.4 |
| | | | 11T | 49.37 | 35.97 |
| Sep-26 | 13 | 21 | 2T | 37.72 | 28.9 |
| | | | 4T | 88.79 | 65.9 |
| | | | 6T | — | — |
| | | | 8T | — | — |
| | | | 10T | — | — |
| | | | 11T | — | — |
| Oct-01 | 14 | | 2T | 69.00 | 51.6 |
| | | | 4T | 95.34 | 68.03 |
| | | | 6T | — | — |
| | | | 8T | — | — |
| | | | 10T | — | — |
| | | | 11T | — | — |

Note:
[1]Concentration of fenbendazole (ppm) in feed samples obtained from ESC curve;
[2]Concentration of fenbendazole (ppm) in feed samples obtained from MMC curve.
— indicates that there was no feed remaining at that site for analysis.

TABLE V ppm Fenbendazole remaining in medicated feed during field sampling period

| Sampling Period | ppm Fenbendazole Remaining |
|---|---|
| 1 | 72.66 |
| 2 | 70.11 |
| 3 | 73.58 |
| 4 | 45.63 |
| 5 | 73.57 |
| 6 | 97.21 |
| 7 | 63.01 |
| 8 | 73.46 |
| 9 | 63.00 |
| 10 | 64.95 |
| 11 | 85.33 |
| 12 | 75.16 |
| 13 | 63.25 |
| 14 | 82.17 |

Conclusion: As indicated by data in Tables IV and V, fenbendazole in composition 10 demonstrated excellent stability in field conditions. Despite temperatures ranging from 18-38° C. during the study period, no considerable degradation of fenbendazole in feed was observed. On average, approximately 75% fenbendazole concentration remained in composition 10 after 4 days of field conditions. Analysis of composition 10 from field studies indicates the fenbendazole concentration on the surface of composition 10 degraded first, but the concentration of fenbendazole inside composition 10 was stable. This was expected, because fenbendazole breaks down readily in ultra violet radiation.

Fenbendazole is known to be stable from 4.4-37.7° C. and in 10-100% humidity as long as it is protected from photo oxidation, such as in composition 10. Analysis of composition 10 in storage indicates concentration of fenbendazole is 50 ppm after 6 months. This data, combined with Stability Test 1, indicate composition 10 is stable within a wide range of temperature and humidity ranges in corresponding ecoregions.

Stability Test 2—Integration of Fenbendazole Into Composition 10 Matrix

Tests were performed to determine whether or not fenbendazole was on the surface or inside the composition 10 feed matrix by extracting fenbendazole from composition 10 feed granules. Concentration of fenbendazole in composition 10 granules was found to be 52.42±13.73 ppm inside composition 10. Thus, fenbendazole in the composition 10 granule interior is protected.

Stability Test 3: Exposure of Composition 10 to Elevated Temperatures

Composition 10 was exposed to elevated temperature (75° C.) for 1 hour to determine if fenbendazole inside composition 10 was being protected from the effects of high temperature. Control composition 10 was left at room temperature for the same time period. Additionally, 100 ppm fenbendazole in acetonitrile was used as a positive control and exposed to the same conditions (room and elevated temperature for 1 hour).

TABLE VI

Fenbendazole Concentration in Composition 10 and 100 ppm Fenbendazole solution at elevated temperature

| Temp ° C. | Fenbendazole extracted from composition 10 (ppm) | Fenbendazole extracted from 100 ppm fenbendazole solution (ppm) |
|---|---|---|
| 21 | 40.75 ppm | 115.18 ppm |
| 75 | 47.58 ppm | 93.36 ppm |

A decrease in the concentration of fenbendazole extracted from 100 ppm fenbendazole exposed to a temperature of 75° C. suggests that fenbendazole is prone to thermal degradation at extremely high temperatures. More importantly, a slightly higher concentration of fenbendazole was extracted from composition 10 exposed to 75° C.

To investigate the increase in the amount of fenbendazole extracted from composition 10 exposed to 75° C., the amount of moisture in composition 10 was determined by the Association of Official Agricultural Chemists. It was observed that composition 10 has a moisture content of 10.4 ppm, by weight. Heating composition 10 at 75° C. for 1 hour would have resulted in a decrease in moisture content of composition 10. This increases the accessibility of extracting solvent to fenbendazole in composition 10, which supports fenbendazole is inside the matrix and not on the surface, of composition 10.

At temperatures observed in field conditions in West Texas, an extremely small amount of thermal degradation was observed, probably directly related to the incorporation of fenbendazole in the interior of the composition 10 granule feed vs. being on the granular surface. At extremely high temperatures, such as 75° C. some thermal degradation was observed, but these temperatures are not seen under standard field conditions.

Conclusion: Stability Studies provide strong evidence that fenbendazole is incorporated into the interior of the composition 10 granules and that fenbendazole concentration in composition 10 is stable in the field.

Product By Process and Method of Preparation

The present invention provides a method for preparing a composition for treating parasitic nematode infections in wild birds. An exemplary embodiment is depicted in FIGS. 1-6.

Figure 2:
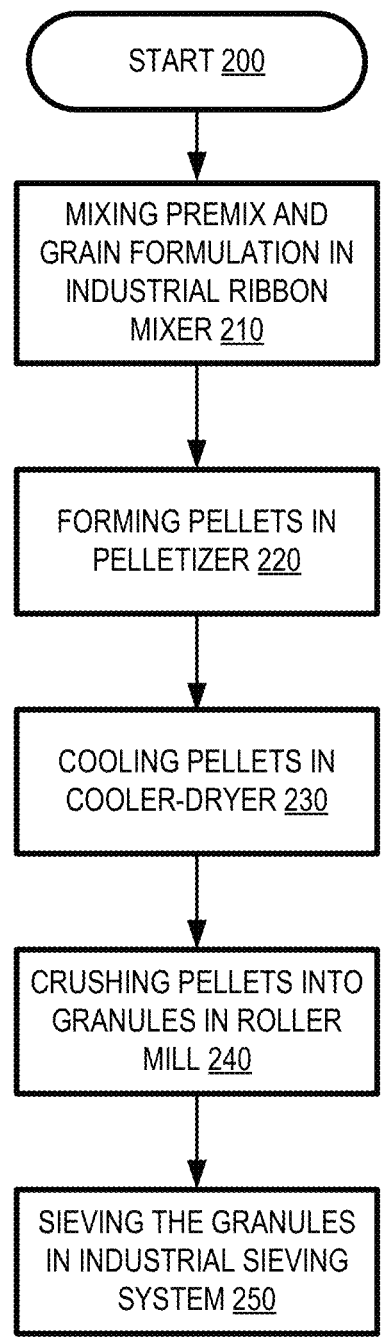
FIG. 2 is a flow diagram for illustrating the steps of a method of preparing the composition for treating parasitic nematode infections, according to embodiments of the present invention.

At step 210, in FIG. 2, (i) a fenbendazole premix 12 comprising about 20,000 ppm, a solvent, a solubilizing agent, and a premix grain carrier, (ii) a grain formulation 14, having a plurality of grains selected from the group consisting of ground corn, soybean meal, whole milo, wheat midds, and rice bran, and (iii) an optional layer premix 15 enters a suitable feed mill 16, including an industrial ribbon mixer.

Figure 3:
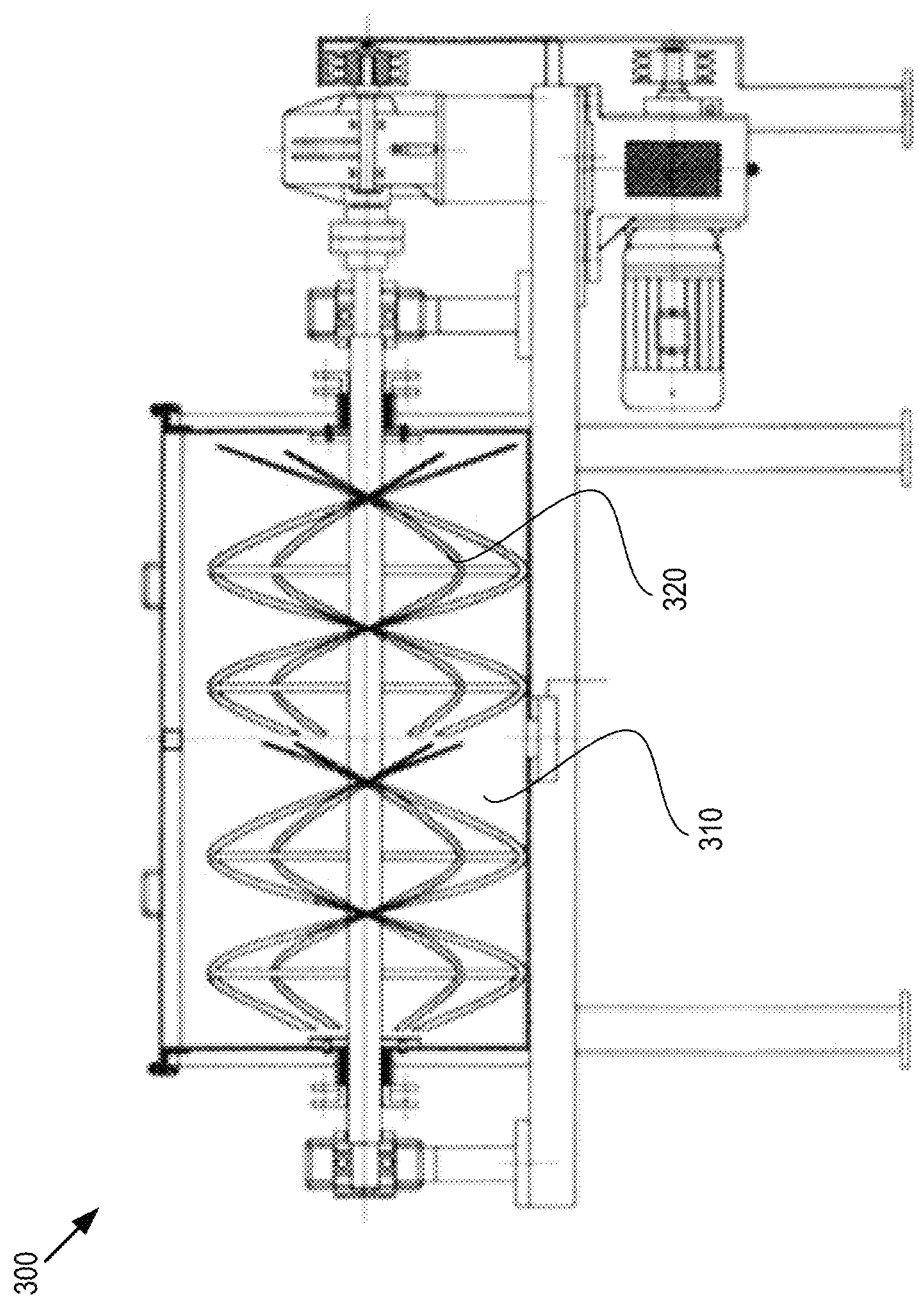
FIG. 3 illustrates an industrial ribbon mixer suitable for carrying out certain steps of the method of FIG. 2.
Figure 4:
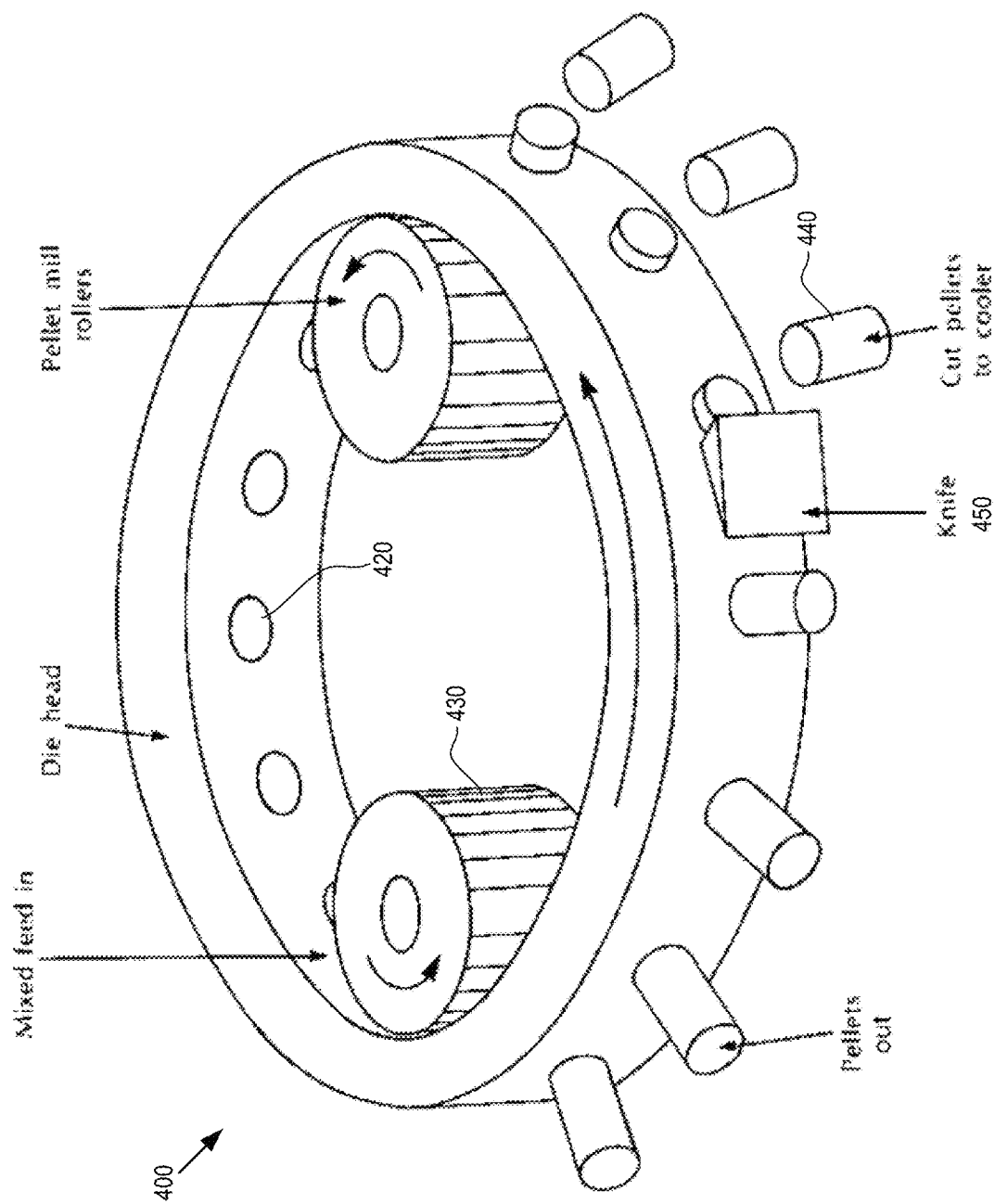
FIG. 4 illustrates an industrial pellet mill die suitable for carrying out certain steps of the method of FIG. 2.

A suitable industrial ribbon mixer 300 is depicted in FIG. 3. Ribbon mixers 300 are known in the animal feed industry for their ability to ensure homogeneous blends. Ribbon mixer 300 may include a U-shaped horizontal trough 310 and helical ribbon agitator 320 rotating within. Ribbon mixers 300 provide a triple mixing action ensuring fast, efficient blending. The dimensions and configuration of the helical ribbon agitators 320 are balanced to provide movement of material within trough 310 that avoids dead spots and gives rapid product discharge. Ribbon mixing fully integrates the fenbendazole within the grain formulation 14 and optional layer premix 15, thereby yielding a mixture with fenbendazole concentration of between 80 ppm and 120 ppm.

At step 220 of FIG. 2, the mixture exits ribbon mixer 300 as a soft, blended mixture and is automatically sent to a suitable animal feed pelletizer to be converted into pellets. A feed pelletizer typically contains a pelletizing chamber die 400, depicted in FIG. 4. The general pelletizing process involves passing the mixture through a conditioning chamber where steam is added, increasing the moisture and temperature. During subsequent compression and extrusion, friction further increases temperature. The pelletizer forces the now soft mixture through holes 420 in pelletizing chamber die 400. Rolls 430 mounted inside the die ring turn on a rotating shaft as friction develops (due to the presence of composition 10 between roll and die). The mixture is forced through the die holes 420 in increments, so that dissection of a finished pellet shows tight layers of mixture. Extruded pellets 440 of appropriate lengths are cut off by knives 450 mounted on the inside of the die casing. In a preferred embodiment, the mixture discharges the pelletizer as 0.5 cm pellets 440.

Figure 5:
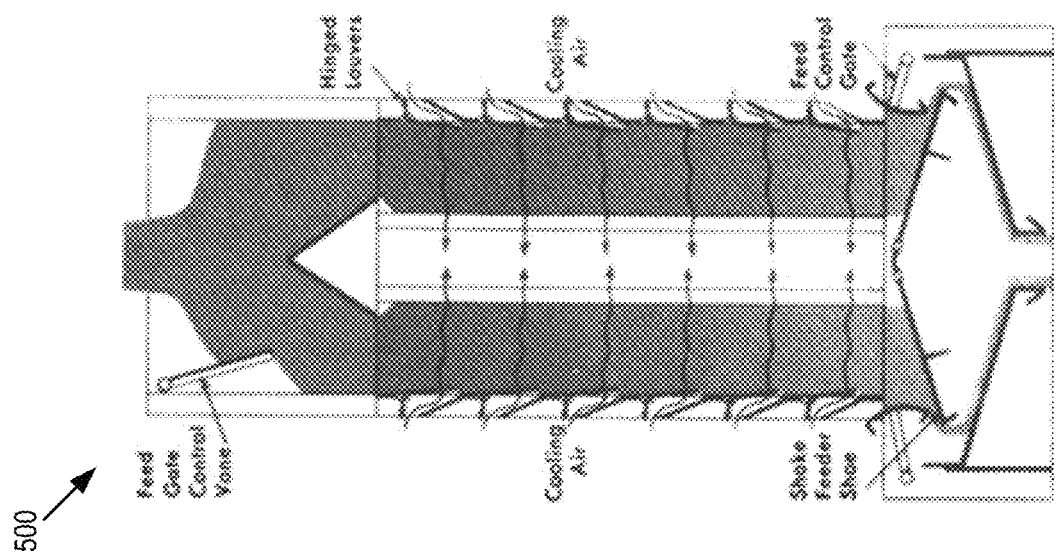
FIG. 5 illustrates an industrial pellet cooler suitable for carrying out certain steps of the method of FIG. 2.

At step 230 of FIG. 2, pellets 440 enter a cooler-dryer. Referring now to FIG. 5, a vertical cooler-dryer 500 is depicted, wherein pellets 440 are discharged from the pelletizer into the top of a flat-sided hopper and dropped into an attached cooling bin. This is divided in the middle with a plenum connected to the suction side of a blower fan. The weight of pellets 440 filling the cooler pivots perforated louvers on the two sides to allow cool air to permeate the hot pellets 440, removing moisture, and cooling the pellets 440 before entering the plenum for discharge through the blower. Pellets leave the bin at the bottom via discharge gates at a rate regulated by the amount of hot pellets 440 entering the cooler. This ensures uniform cooling and drying of pellets 440. The temperature imparted to pellets 440 in the process of their manufacture assists the removal of moisture by the air-drying process. Generally, within ten minutes after extrusion, hard pellets 440 are cooled to ambient temperature and brought to a moisture content slightly above that of the entering soft mixture. Specifically, according to embodiments of the present invention, the mixture discharges as 0.5 cm pellets 440 onto a vertical screened hopper and are air-cooled to slightly above ambient temperatures and dried to below 15% moisture.

Figure 6:
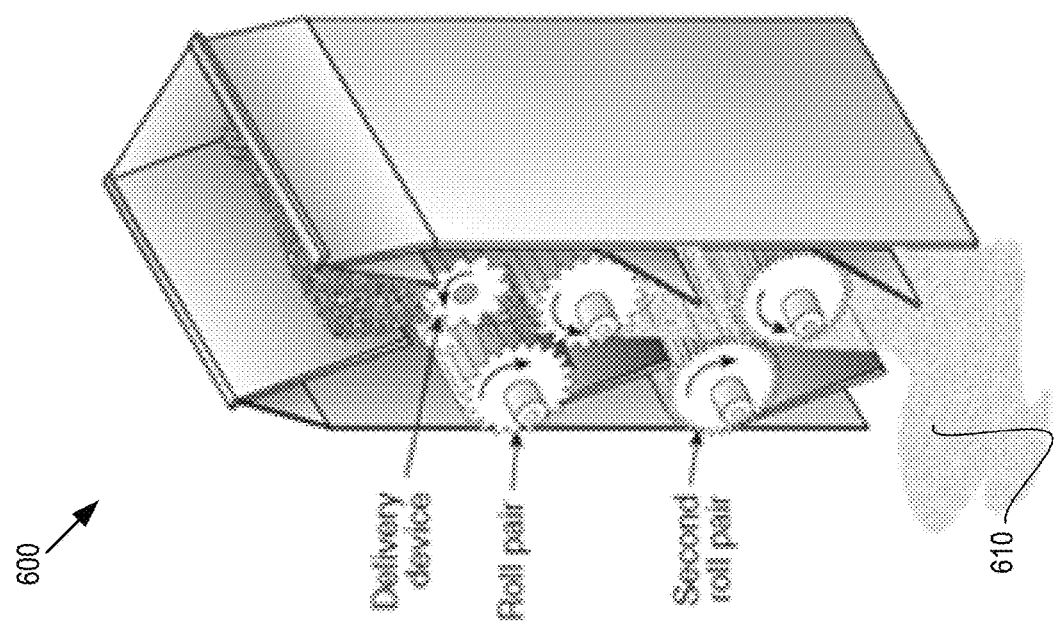
FIG. 6 illustrates an industrial roller mill suitable for carrying out certain steps of the method of FIG. 2.

At step 240 of FIG. 2, cooled pellets 440 are sent through an elevator leg to a roller mill 600, depicted in FIG. 6, for grinding into granules 610. A combination of cutting, attrition, and crushing occurs in roller mill 600. Roller mill 610 uses smooth or corrugated rolls rotating at the same speed set at a pre-determined distance apart with material passing between them. A tearing action may be added by operating the rolls at different speeds and by corrugations which are different for each roll; i.e., the top roll may have off-radial spiral corrugations and the bottom roll lateral corrugations. This last type is used in making granules 610 from hard pellets 440, as it provides a breaking surface without much impact, resulting in very little to no dust. Utilizing the already extremely well-mixed mixture, the roller mill discharges a medium sized granule 610.

Next, at step 250 of FIG. 2, granules 610 may be sent to an industrial sieving system to classify granules 610 into a desired size. Granules 610 larger than a desired specified size may be re-ground or rejected. Granules 610 passing through the industrial sieving system may be selected to comply with preferred granule size 610 for a targeted wild bird species. Preferably, for wild bobwhite quail, the granules 610 may have a diameter of between about 0.3 mm and about 0.13 mm, a surface area of between about 0.407 square mm and about 0.30 square mm, or a diameter greater than about 150 microns. Granules 610 passing through the industrial sieving system contain very little dust and/or fines and may be sent to a bagger system.

Analytical chemistry reveals fenbendazole incorporation into granules 610 is consistently within acceptable ranges of the 100 ppm target for wild bobwhite quail as discussed herein above. Further, the disclosed method of preparation produces granules 610 with very little dust in order to reduce distribution of the fenbendazole in a wild environment. Therefore, the disclosed method of preparation produces the disclosed composition with fenbendazole incorporated ready for introduction into a wild environment.

Based on this disclosure, a person skilled in the art will appreciate the general approach to be taken in preparing the compositions of this invention.

Method of Treatment

With reference to FIGS. 7-8, a method of treating parasitic nematode infections in wild birds is described herein below.

Referring now to FIG. 7, for wild birds, such as wild bobwhite quail for example, exemplary system 700 may be a generally rectangular structure having a roof and sides for installing in a wild bird habitat. Entrances 760 are sized to prevent non-targeted wild and domesticated animals from entering system 700 to eat or disturb composition 10 but to allow wild bird species to walk in, feed, and then walk out. System 700 includes a call bird 760 and a feeder 770 protected from the environment by a cover 720 (if required).

Once inside system 700, a targeted species readily feeds on composition 10 provided in feeder 770. Feeder 770 provides continual supply of composition 10 to the targeted wild birds. Feeder 770 may be a conventional, commercially available feeder, such as those commonly used for feeding wild game birds. In an embodiment, wild birds habituated to feeding in system 700 can readily be provided composition 10 for parasite or disease control at any time. A prior evaluation of infection levels in the targeted species, for example wild birds such as wild bobwhite quail, determines when and where to provide composition 10 in systems 700.

Referring now to FIG. 8, a flow diagram of an exemplary method of treating wild birds for parasitic nematode infections is depicted. The method of treatment starts at step 800. At step 810, samples from wild birds are collected. At step 820, the collected samples are tested to determine if the targeted wild birds are infected with parasites or another disease being investigated. At step 830, if testing shows that there are parasites or other diseases, treatment solution options are formulated at step 840. If no parasites or diseases are found in the collected samples, the method returns to step 810, involving sampling of the targeted wild birds at a later time.

At step 850, the number of needed treatment systems 700 and locations on site 800 are determined by conducting a survey of the site. Factors included in determining how many and where system(s) 700 are placed include the targeted species, terrain topology, prevailing wind directions, and ambient noise level. Generally, one treatment system per section of land (or per square mile) should be adequate. Camera surveillance in the treatment system can provide detailed information on bird use in terms of numbers, time, and frequency of visits, if desired.

At step 860, system(s) 700 are installed. System 700 is preferably installed adjacent to adequate ground habitat to protect the wild birds from predators and is preferably located to the east of standing vegetation (e.g. salt cedar and mesquite trees), so that shade can be provided for the summer afternoon sun. In an embodiment for treating wild bobwhite quail, systems 700 are preferably deployed in late winter or early spring to facilitate habituation of the wild birds to come to the treatment system 700 for feeding so that medicated feed can be delivered easily to the targeted birds at a later time.

At step 870, feeder 770 is charged with a medicated feed, composition 10, for example. Composition 10 includes fenbendazole premix 12 comprising about 20,000 ppm fenbendazole, a solvent, a solubilizing agent, and a premix grain carrier. Composition 10 further includes grain formulation 14 having a plurality of grains selected from the group consisting of ground corn, soybean meal, whole milo, wheat midds, and rice bran. Composition 10 optionally includes layer premix 15. Fenbendazole premix 12 is integrated within composition 10 thereby yielding a fenbendazole concentration of between 80 ppm and 120 ppm in composition 10.

At step 880, system(s) 700 are monitored in person or remotely via cameras or other electronic means having the capability to transmit the pictures to a central observation office.

The method returns to step 810, sampling of wild birds to determine if the parasites are controlled in the targeted bird species. The sampling of birds after medicated feed treatment can occur promptly after the treatment period (estimated 2 weeks to 1 month) is concluded.

It will be appreciated by persons skilled in the art that numerous variations and/or modifications may be made to the invention as shown in the specific embodiments without departing from the scope of the invention as broadly described. The present embodiments are, therefore, to be considered in all respect as illustrative and not restrictive.

As used herein, the terms comprises, comprising, or any other variation thereof, are intended to cover a non-exclusive inclusion, such that a process, method, article, or apparatus that comprises a list of elements does not include only those elements but may include other elements not expressly listed or inherent to such process, method, article, or apparatus. Further, no element described herein is required for the practice of the invention unless expressly described as essential or critical.

As used herein, the terms "or" is intended to cover a non-exclusive inclusion. That is, "or" includes both meanings of both "or" and "and/or."

The terminology used herein is for the purpose of describing particular embodiments only and is not intended to be limiting of the invention. As used herein, the singular forms "a", "an" and "the" are intended to include the plural forms as well, unless the context clearly indicates otherwise.

The corresponding structures, materials, acts, and equivalents of all means or step plus function elements in the claims below are intended to include any structure, material, or act for performing the function in combination with other claimed elements as specifically claimed.

It should be appreciated that the particular implementations shown and described herein are illustrative of the invention and are not intended to otherwise limit the scope of the present invention in any way. Other variations are within the scope of the following claims. Those skilled in the art having read this disclosure will recognize that changes and modifications may be made to the embodiments without departing from the scope of the present invention.

While this specification contains many specifics, these should not be construed as limitations on the scope of the invention or of what can be claimed, but rather as descriptions of features specific to particular implementations of the invention. Certain features that are described in this specification in the context of separate implementations can also be implemented in combination in a single implementation. Conversely, various features that are described in the context of a single implementation can also be implemented in multiple implementations separately or in any suitable sub combination. Moreover, although features can be described above as acting in certain combinations and even initially claimed as such, one or more features from a claimed combination can in some cases be excised from the combination, and the claimed combination can be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the implementations described above should not be understood as requiring such separation in all implementations.

The flowchart and block diagrams in the drawings illustrate the architecture, functionality, and operation of possible implementations of compositions, systems and methods, according to various embodiments of the present invention.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of any or all the claims.

What is claimed is:

1. A composition consisting of:
   i. a grain formulation consisting of a plurality of grains selected from a group consisting of ground corn, soybean meal, whole milo, wheat midds, and rice bran; and
   ii. a fenbendazole premix consisting of:
   a) about 200,000 ppm fenbendazole,
   b) a solvent selected from a group consisting of mineral oil, soybean oil, and peanut oil, wherein the solvent attaches to the solubilizing agent for distributing and stabilizing the fenbendazole throughout the fenbendazole premix,
   c) about 350,000 to 480,000 ppm of a calcium carbonate solubilizing agent suitable for integrating into matrices of the fenbendazole, and d) a premix grain carrier, wherein the premix grain carrier comprises roughage products and facilitates mixing of the fenbendazole premix within the grain formulation, wherein the composition:
a) has a fenbendazole concentration of between 80 ppm and 120 ppm;
b) is capable of treating parasitic nematode infections in wild birds;
c) is in the form of granules; and
d) is capable of retaining fenbendazole stability in a natural habitat for a sufficient period of time for the wild birds to ingest the composition at will in order to treat the parasitic nematode infections in the wild birds.

2. The composition of claim 1, wherein the granules have a diameter of between about 0.3 mm and about 0.13 mm.

3. The composition of claim 1, wherein the granules have a surface area of between about 0.407 square mm and about 0.30 square mm.

4. The composition of claim 1, wherein the granules have a diameter greater than about 150 microns.

5. The composition of claim 1, wherein the parasitic nematode is *Oxyspirura petrowi*.

6. The composition of claim 1, wherein the parasitic nematode is *Aulonocephalus* spp.

7. The composition of claim 1, wherein the parasitic nematode is *Heterakis* spp.

8. The composition of claim 1, wherein the parasitic nematode is *Capillaria* spp.

9. The composition of claim 1, wherein the wild birds are members of order Galliformes.

10. The composition of claim 1, wherein the wild birds are members of order Passeriformes.

11. The composition of claim 1, wherein the wild birds are *Colinus virginianus*.

12. The composition of claim 1, wherein the wild birds are *Callipepla squamata*.

* * * * *